US012807919B2

(12) United States Patent
Gilligan et al.

(10) Patent No.: US 12,807,919 B2
(45) Date of Patent: Nov. 24, 2026

(54) SYSTEM AND METHOD FOR CULTIVATING BIOLOGICAL CELL CULTURES

(71) Applicant: AIXINNO LIMITED, Cambridge (GB)

(72) Inventors: Patrick Clemente Gilligan, Cambridge (GB); Kenneth B. K. Teo, Cambridge (GB); John Edward Connah, Cambridge (GB); David Anthony Bullinaria, Bluntisham (GB)

(73) Assignee: AIXINNO LIMITED, Cambridge (GB)

( * ) Notice: Subject to any disclaimer, the term of this patent is extended or adjusted under 35 U.S.C. 154(b) by 576 days.

(21) Appl. No.: 18/279,502

(22) PCT Filed: Mar. 14, 2022

(86) PCT No.: PCT/EP2022/056442
§ 371 (c)(1),
(2) Date: Aug. 30, 2023

(87) PCT Pub. No.: WO2022/194730
PCT Pub. Date: Sep. 22, 2022

(65) Prior Publication Data

US 2024/0150704 A1 May 9, 2024

(30) Foreign Application Priority Data

Mar. 19, 2021 (DE) ..................... 10 2021 106 852.5
Dec. 14, 2021 (DE) ..................... 10 2021 133 108.0

(51) Int. Cl.
*C12M 1/36* (2006.01)
*C12M 1/00* (2006.01)
(Continued)

(52) U.S. Cl.
CPC ............ *C12M 41/48* (2013.01); *C12M 23/44* (2013.01); *C12M 23/58* (2013.01); *C12M 29/06* (2013.01); *C12M 41/32* (2013.01); *C12M 41/36* (2013.01)

(58) Field of Classification Search
CPC ...... C12M 41/48; C12M 41/32; C12M 41/36; C12M 23/58; C12M 23/44; C12M 23/50; C12M 29/06
See application file for complete search history.

(56) References Cited

U.S. PATENT DOCUMENTS

2005/0260743 A1 11/2005 Drake et al.
2019/0033819 A1 * 1/2019 Chao ..................... G05B 19/31
(Continued)

FOREIGN PATENT DOCUMENTS

EP 1 598 415 A1 11/2005
WO 2019/241885 A1 12/2019
(Continued)

OTHER PUBLICATIONS

International Search Report mailed Aug. 8, 2022, from the ISA/European Patent Office, for International Patent Application No. PCT/EP2022/056442 (filed Mar. 14, 2022), 7 pgs.
(Continued)

*Primary Examiner* — Michael L Hobbs
(74) *Attorney, Agent, or Firm* — Ascenda Law Group, PC

(57) ABSTRACT

Biological cells, which are stored on carriers in a storage module, are cultivated in a process module. Each cell line is assigned an application containing a treatment specification, which contains one or more workflows that are performed in the process module at successive time intervals, each with a respective start time. Each workflow contains a work step or a plurality of work steps to be performed in succession. The control device controls the parallel execution of a plurality
(Continued)

of applications and starts the one or more workflows of the different applications one after another in the same process module. In order to economically perform the workflows successively in a single process module, each workflow is assigned an effective function dependent on the start time, and the sequence and the start times of the workflows of different applications are determined by minimizing or maximizing the sum of the effective functions.

14 Claims, 5 Drawing Sheets

(51) Int. Cl.

| | |
|---|---|
| ***C12M 1/34*** | (2006.01) |
| ***C12M 3/00*** | (2006.01) |

(56) References Cited

U.S. PATENT DOCUMENTS

| | | | | |
|---|---|---|---|---|
| 2020/0283713 | A1 | 9/2020 | Ball et al. | |
| 2022/0290091 | A1 * | 9/2022 | Abraham | G16H 40/63 |

FOREIGN PATENT DOCUMENTS

| | | | |
|---|---|---|---|
| WO | 2020/098957 | A1 | 5/2020 |
| WO | 2020/098960 | A1 | 5/2020 |

OTHER PUBLICATIONS

Written Opinion mailed Aug. 8, 2022, from the ISA/European Patent Office, for International Patent Application No. PCT/EP2022/056442 (filed Mar. 14, 2022), 8 pgs.

Written Opinion of the International Searching Authority mailed Aug. 8, 2022, from the ISA/European Patent Office, for International Patent Application No. PCT/EP2022/056442 (filed Mar. 14, 2022), English translation, 8 pp.

Written Opinion of the International Preliminary Examination Authority mailed Mar. 17, 2023, from the IPEA/European Patent Office, for International Patent Application No. PCT/EP2022/056442 (filed Mar. 14, 2022), 20 pp.

International Preliminary Report on Patentability issued Jun. 20, 2023, from the IPEA/European Patent Office, for International Patent Application No. PCT/EP2022/056442 (filed Mar. 14, 2022), 16 pp.

* cited by examiner

Fig. 1
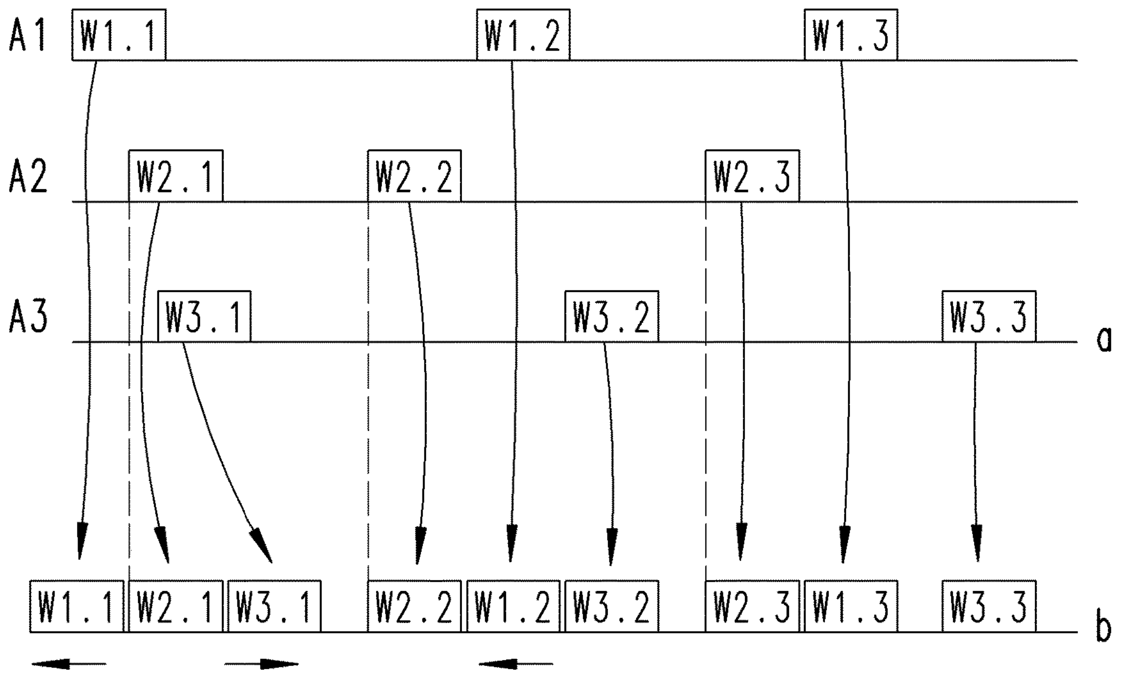
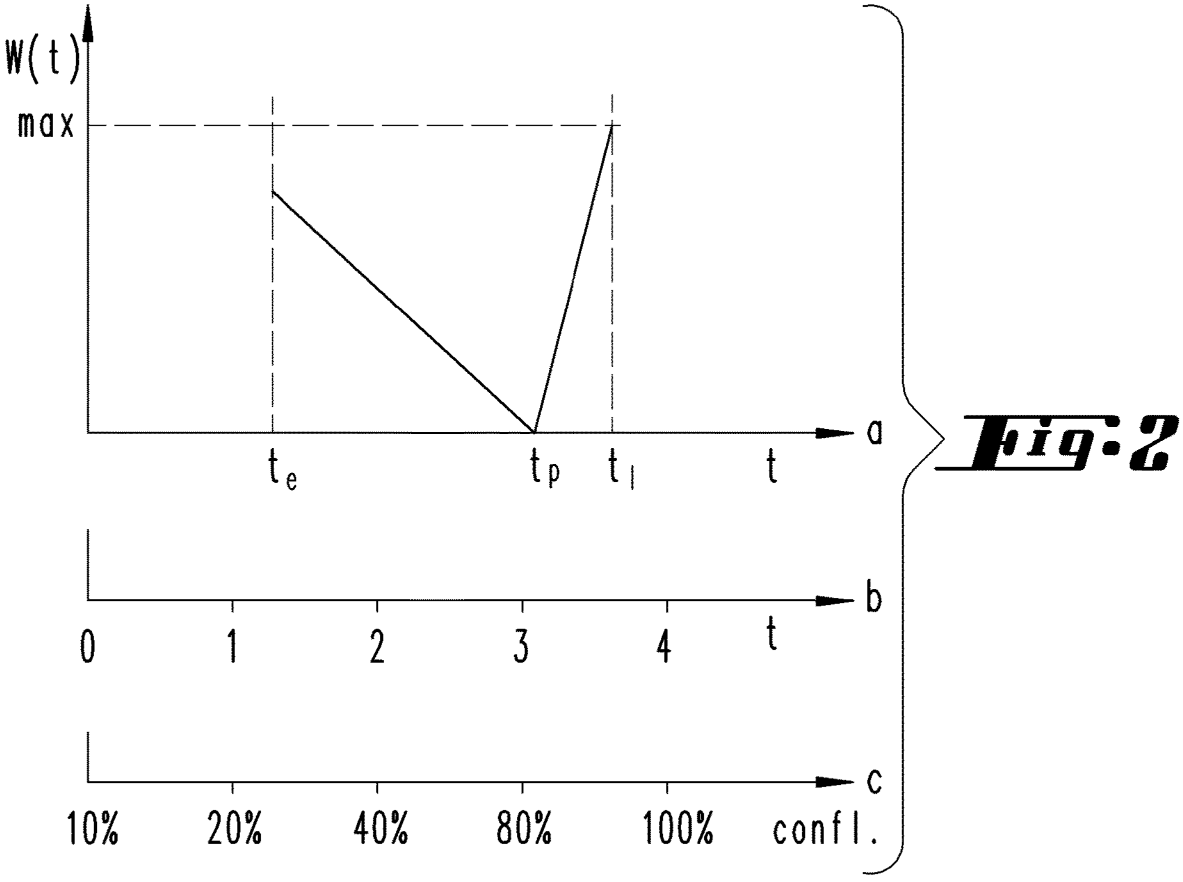
Fig. 2

Fig. 3
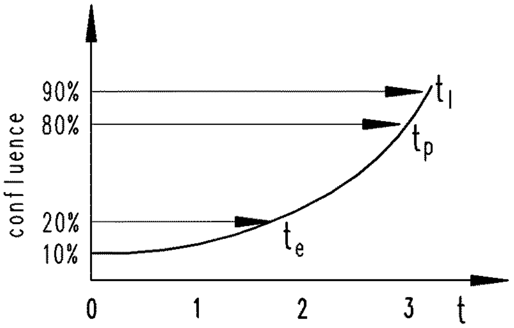
Fig. 4
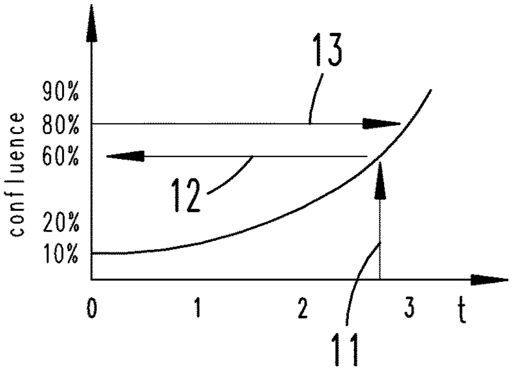
Fig. 5
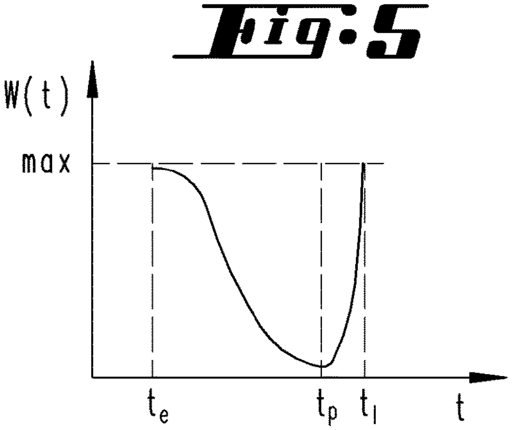
Fig. 6
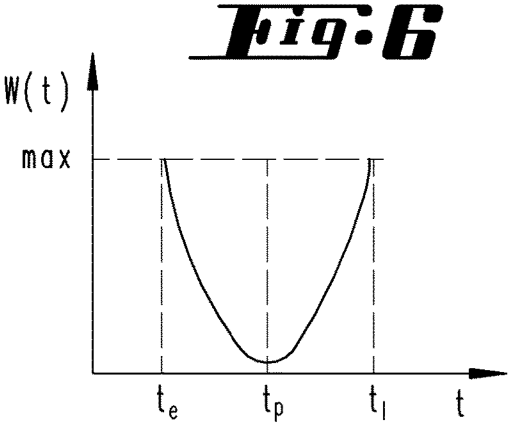
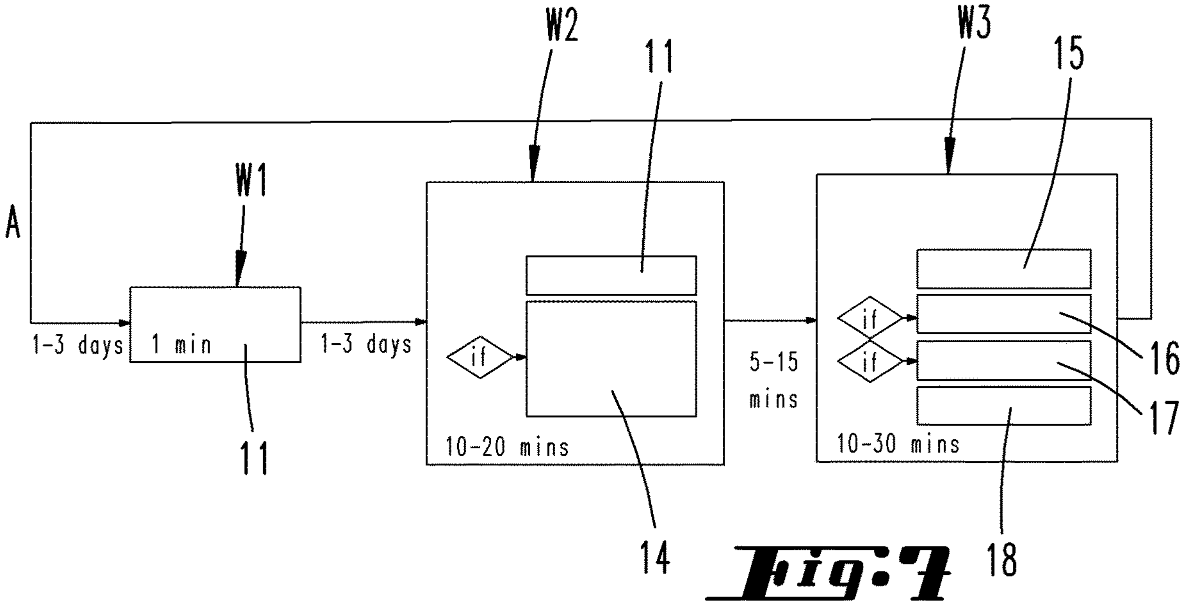
Fig. 7

Fig. 10
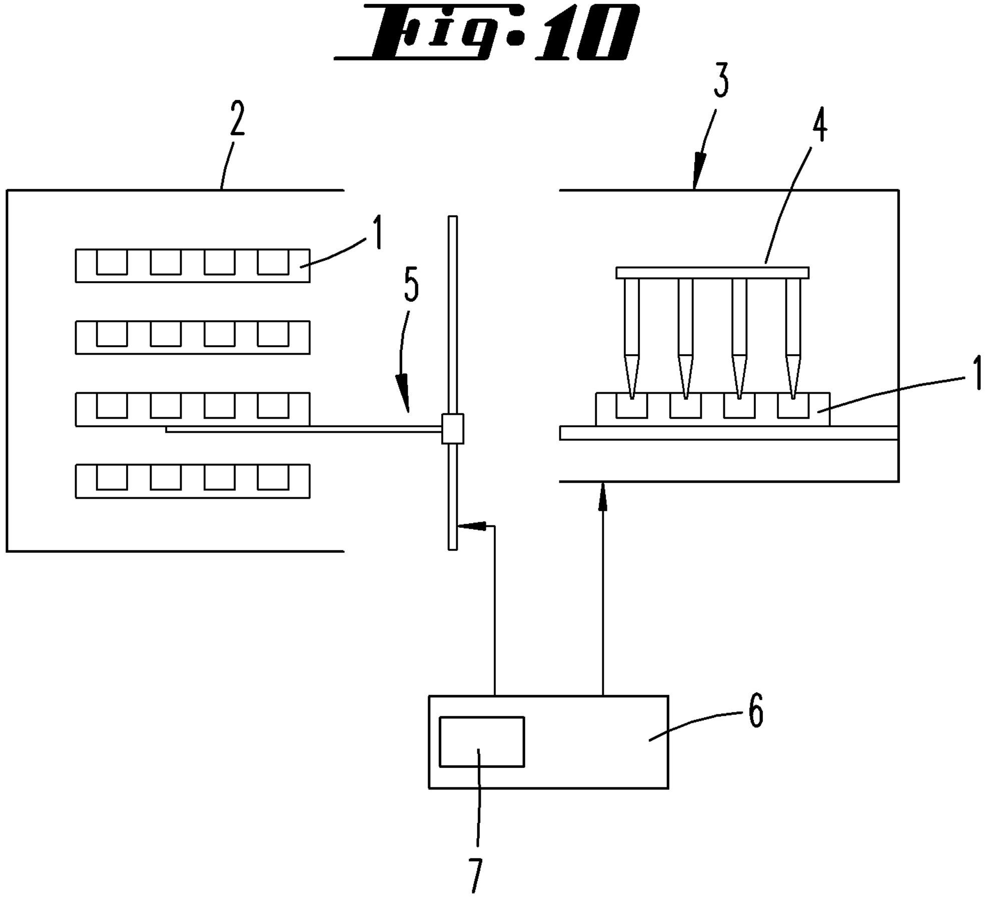
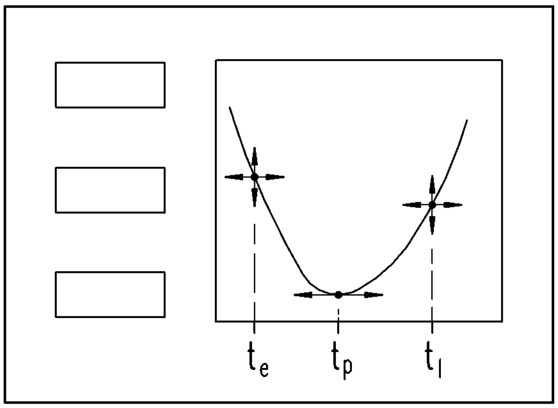
Fig. 11

Fig. 12
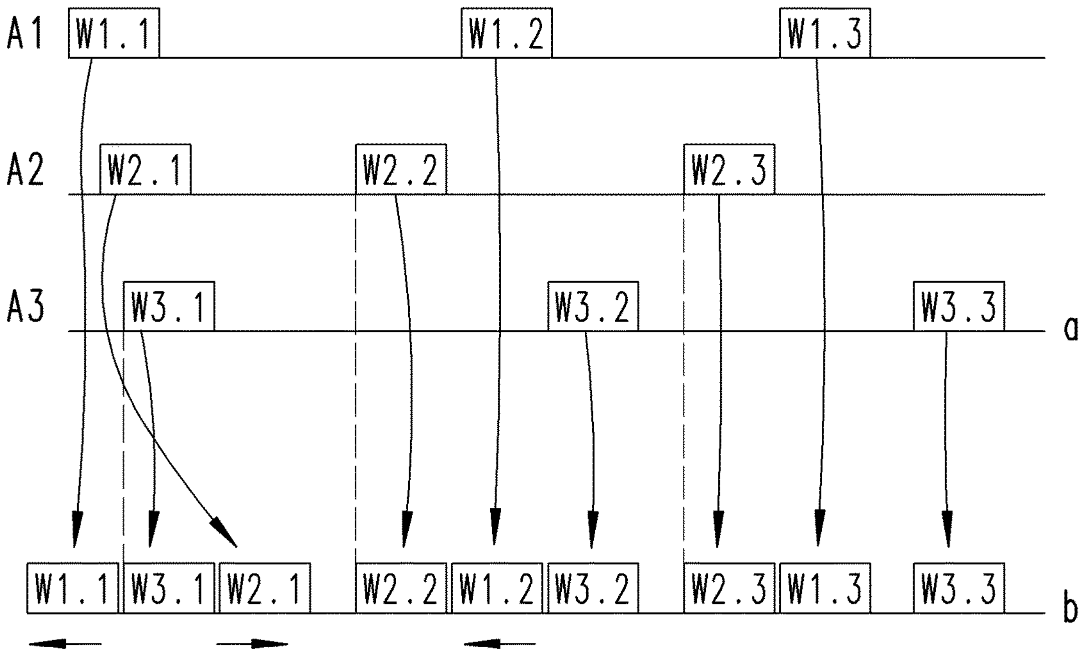
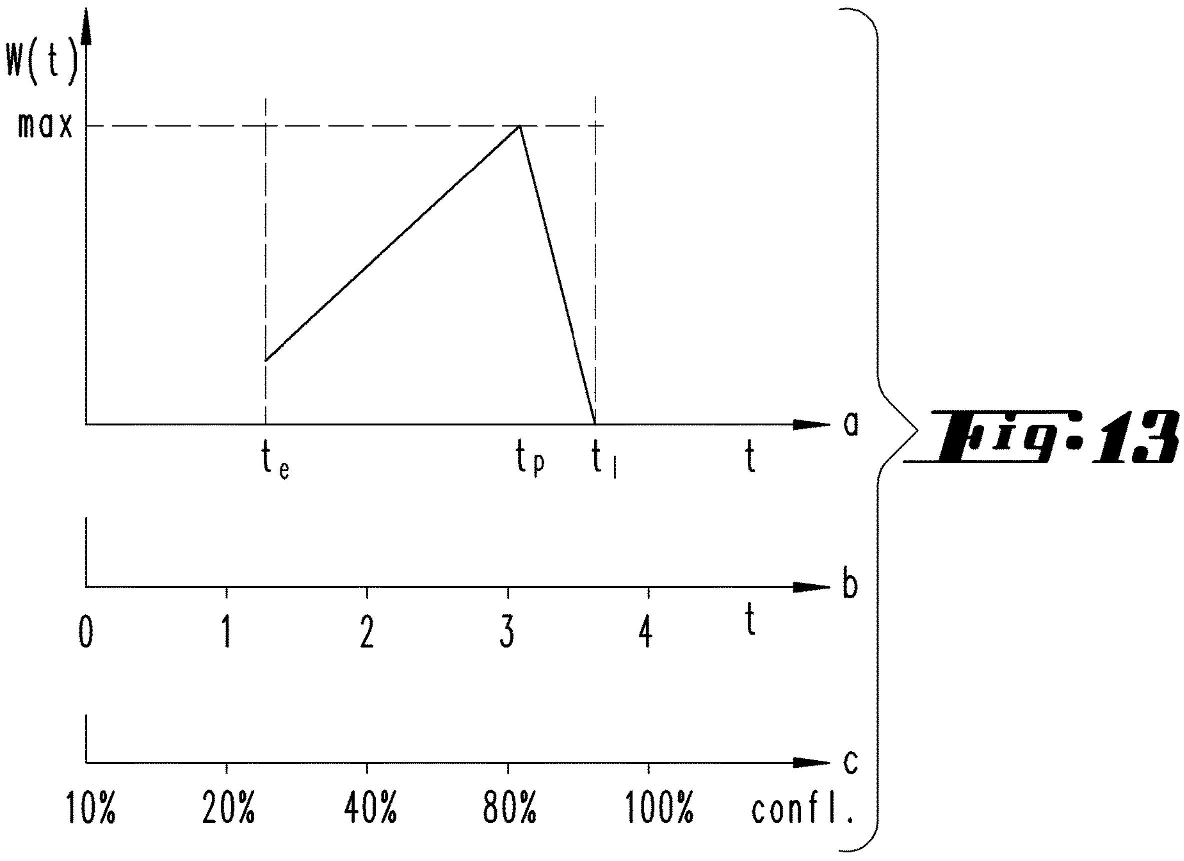
Fig. 13

SYSTEM AND METHOD FOR CULTIVATING BIOLOGICAL CELL CULTURES

RELATED APPLICATIONS

This application is a National Stage under 35 USC 371 of and claims priority to International Application No. PCT/EP2022/056442, filed 14 Mar. 2022, which claims the priority benefit of DE Application No. 10 2021 106 852.5, filed 19 Mar. 2021 and DE 10 2021 133 108.0, filed 14 Dec. 2021.

FIELD OF THE INVENTION

The invention relates to a system or a method for cultivating biological cell cultures, with a plurality of carriers, which each carry one or more cell cultures, with at least one storage module, in which the carriers are stored, with a process module, in which the cell cultures carried by the carriers are treated by means of at least one treatment device, with a transport device, with which the carriers are transported between the storage module and the process module, and with a programmed or programmable control device, which has a memory device and which controls the transport device and the treatment device, wherein applications assigned to several different cell cultures are stored in the memory device, wherein each application is a treatment specification for treating the assigned cell culture, which contains one or more treatment units, hereinafter referred to as workflows, which are performed at time intervals successively at a respective start time in the process module, wherein a workflow contains one or more work steps, wherein the one or more work steps must be performed immediately one after the other, wherein the control device controls the simultaneous performance of a plurality of applications, and thereby starts one or more workflows of the different applications in chronological sequence one after the other in the same process module.

BACKGROUND

Cells, in particular human cells, are grown in plastic trays, for example in troughs of carriers, by adding nutrients. Adherent cells are typically grown in a monolayer, which adheres to the bottom of a plastic tray or a trough in a carrier. Cells like these are detached from the bottom before the entire bottom is covered with the cells. A confluence scan is performed for this purpose, with which the degree to which a substrate, for example the bottom of a carrier, is covered with cells. The cells detached from the bottom can be diluted and transferred to new carriers or into new troughs. Systems and methods in prior art for maintaining such cell cultures can have an incubator, a robot for handling the carriers that carry the cells, and treatment devices, with which the nutrient medium can be added or changed.

EP 1 598 415 A1 describes a system for cultivating biological cell cultures, in which cells are stored on carriers in a storage module. A transport device comprising a gripper can be used to remove the carriers from the storage module and transport them into a process module. The cell cultures stored on the carrier are there treated by means of a treatment device. Different types of cell cultures are treated according to different treatment specifications. Each cell culture, for example each carrier, can have an application, which is a treatment specification for treating the assigned cell culture. This type of application can contain one or more workflows. Each workflow can contain at least one work step. However, a workflow can also have several work steps. The work steps of a workflow are characterized in that they must be performed immediately or in short succession. In contrast, the several workflows of an application are each performed in larger time intervals between individual workflows. Between the performance of individual workflows, the carriers can be located in storage spaces assigned to them in the storage module. The applications, which can number 100 or more, and the workflows assigned to them can be stored in a memory device of a control device as digital datasets. The programmable control device coordinates the parallel performance of a plurality of applications, and controls the one or more workflows of the different applications one after the other in chronological order in the same process module.

An automated system for the performance of these applications, which preferably contain at least one or more workflows, in which the nutrient medium is changed or a confluence is measured, are controlled by a planning program of the control device. This type of planning program generates a timetable for performing the workflows of the individual applications one after the other. In addition, the planning program should be able to influence the workflows. In general, this type of timetable contains several work processes, in which the duration of the work processes and the intervals between the work processes can vary unpredictably. Since cells are living units and their properties, in particular growth rates, can vary unpredictably, the work processes must be adjusted to the respective individual development of the cell culture. In general, the growth rate of cells is variable and hard to predict. For example, the growth rate of the cells can vary from batch to batch due to known factors, such as transfection, serum deficiency or cryptic factors. In particular the behavior of a cell culture must thus be observed so as to adjust time sequences in terms of the workflow start times to the development status of a cell culture.

In addition, a system for cultivating biological cell cultures must be able to perform applications in a time effective manner, and determine the start times of the workflow in such a way that workflows that would fall within the treatment duration of another workflow at an optimal start time are shifted in time in such a way as to be performed one after the other in the process module.

SUMMARY OF THE INVENTION

The object of the invention is to further develop the usefulness of a system or a method for cultivating biological cell cultures, in which applications with workflows are performed simultaneously. In particular, one object is to cost-effectively operate the system.

The object is achieved by the invention indicated in the claims, wherein the subclaims are not only advantageous further developments of the invention indicated in claim 1, but also constitute standalone solutions of the object.

A first aspect of the invention relates to avoiding time collisions of workflows, which under optimal conditions would have overlapping processing times. These types of workflows must be shifted in time in such a way that the start time of one workflow comes after the other workflow has ended. The invention proposes that an effective function that depends on the start time be assigned to each workflow. The effective function or the curve of the effective function can have an extremum at the time when the workflow would preferably be performed. The effective function is thus minimal or maximal, or the curve of the effective function has a minimum or maximum at a time when the workflow would preferably be performed. The minimum of the effective function is preferred. The effective function then rises at earlier times and at later times. The rise can be linear or nonlinear, and rise more weakly in the direction of an earliest start time than in the direction of a latest start time or vice versa. For example, if the workflow is a workflow in which the condition of a cell culture is to be monitored, the workflow can have a work step that involves measuring the degree to which the bottom of a trough in which the cells are stored is covered with the cells. This type of confluence scan can be performed using a microscope and an automatic image analysis. Depending on the degree of coverage, cells can be removed in a subsequent step to diminish the degree of coverage. Liquids can be added to detach the cells from the bottom. The cells can be removed with a pipetting device. At the same time, the degree of coverage can be measured to determine a growth rate individually assigned to the cell culture by comparing a degree of coverage in an earlier measurement with the current degree of coverage taking into account the time elapsed in the meantime. This growth rate measured via the confluence scan can be used to calculate a future time at which the cell culture is to be monitored next in a subsequent workflow. The system calculates a preferred start time. For example, the preferred start time can be a time at which a confluence of 80% is expected based upon the determined growth rate. The system can calculate a latest start time, which lies roughly where a confluence of 90% to 100% is predicted based upon the determined growth rate. A later start time would cause the surface to become overgrown. The system can calculate an earliest start time, for example one lying where the calculated confluence lies between 15% and 30%, preferably at 20%. These boundary values for the earliest start time, the latest start time and the preferred start time are used to construct an effective function that can be standardized, for example has the value 0 at the preferred start time and the value 1 at the earliest start time or latest start time. A function of the preferred start time can be involved. However, it is also possible for this type of effective function to asymptotically rise slowly or quickly to the maximal value in particular at the latest start time, if the preferred start time nears the earliest or latest permissible value. If the system contains applications that each have at least one workflow that based upon its preferred start time would fall within the treatment duration of another workflow, the start times of the two workflows are varied in a variation calculation in such a way that the sum of the two is minimized or has a minimum. If the system contains applications in which several workflows would overlap in terms of the time at which performed, these workflows are subjected to a variation calculation, in which the start times of the workflows are varied in such a way that the sum of all effective functions has a minimum. The minimum can be a local minimum. However, it can also be a global minimum. In particular, it is provided that at least some of the workflows be assigned an earliest start time, before which the workflow must not be started. However, it is also provided that at least some of the workflows have a latest start time, after which the workflow must not be started. It can further be provided that the earliest start time and the latest start time lie directly next to the preferred start time, meaning that the workflow must only be started at the preferred start time. A relevant effective function can be mathematically represented by virtue of it having one or two very steep branches, the slope of which rises quickly as the function nears the earliest or latest start value. In the simplest case, the effective functions can have linearly progressing branches. However, the branches of the effective function can also be represented by a polynomial of a higher degree as well. In a preferred embodiment of the invention, the actual start times of the effective functions for the workflows are selected in such a way as to minimize the sum of the effective functions for the workflows, since the effective function is increased when a workflow is performed at a start time other than the preferred start time. In this way, the effective function can be regarded as a cost function, wherein performing a workflow too early or too late results in a penalty or costs. The goal of the system is to minimize the sum of effective functions or cost functions over the workflows of the applications, i.e., to maximize the time efficiency of the system.

Among other things, the invention also relates to a planning software or a planner for managing several functions with one or more workflows. In an alternative configuration of this type of planner, the functions and the goal of the planner can also be reversed. A function could become maximal at a time when a work process is started. The goal of the system would be to maximize the sum of effective functions over the workflows of the applications so as to maximize the time efficiency of the system.

A workflow can comprise at least one or more of the following work steps: Applying a cell culture, counting the living or dead cells, detaching the cells from the bottom of a trough of a carrier, removing cells of the cell culture to diminish the degree of coverage or the confluence, confluence scan, changing a medium of the cell culture, adding nutrients or discontinuing the cell culture. In particular, it can be provided that the workflows in an application have a broad time distribution, in the sense that the workflows have large time intervals between each other. For example, a workflow can last for 30 minutes. During this time, a confluence scan can be performed, the medium of the cell culture can be changed, or a nutrient can be added. The time between two consecutive workflows can measure a few hours or even several days, wherein the time in between consecutive workflows depends on a growth rate of the cell culture that is calculated continuously or recalculated while performing a respective workflow. For example, during a workflow in which the cell growth is monitored, it can be provided that a confluence scan initially be performed, with which the growth rate is determined based upon the confluence set in the previous workflow. The confluence can subsequently be reduced by removing cells, for example to 10%. The confluence can subsequently be reduced, for example to 10%, by removing, separating, diluting cells, or seeding them in a new carrier. Based upon the ascertained growth rate, the preferred start time ($t_p$) of the ensuing workflow can be determined in such a way that the expected confluence measures 80%. Based upon the ascertained growth rate, the effective function is also redetermined, for example by setting an earliest start time at which the confluence measures 20%, and a latest start time ($t_l$) at which the expected confluence measures 95%.

The work steps within a workflow form time-related sequences, which must be performed one after the other, for example with time intervals of ideally 0 (zero) or at most a few minutes, wherein no other workflow can be interspersed between the work steps. For example, a first work step can involve removing a carrier from the storage module and transporting it to the process module. An ensuing second work step can be a confluence scan, for example, in which the degree of coverage of the cells adhering to the bottom of a tray is determined with optical means. A third step can involve adding a "detachment agent," with which the cells are detached from the bottom of the tray or trough of the carrier. A fourth work step can involve at least partially removing the cells from the nutrient solution in the tray or trough, or transferring a portion of the cells into a free tray or trough. The degree of coverage, i.e., the confluence, can be set with this step. A fifth work step can involve adding nutrient solution. A sixth step can involve transporting the carrier back to the storage module. Each of these work steps can influence the progression of the work function. Additional work steps can involve counting the living and dead cells. This work step can be performed before or after the second work step. In order to cultivate a specific cell line, e.g., CHO cells (Chinese hamster ovary), an instance of application is created which contains the parameters for cultivating this cell line, for example a complete medium recipe, the confluence at which the cells must be passed, a split ratio and the number of carrier plates (dishes). An application can relate to one or more carrier plates. An application relating to several carrier plates, which in turn each have a plurality of trays, troughs or carriers in which cell cultures are stored, has workflows whose length of time exceeds that of applications relating to only one carrier plate. The interval between two workflows essentially depends on the cell line, and primarily on the doubling time or split ratio of the cells of the cell line. The split ratio indicates the degree of cell dilution during each workflow. The doubling time usually varies from cell line to cell line, and hence also from instance to instance of an application for cell line maintenance. There are time-critical workflows that must be performed to prevent the cells from becoming overconfluent.

An application can contain workflows that vary in number and sequence. For example, the maintenance of iPSC's (induced pluripotent stem cells) typically involves a workflow for changing media ("feeding cells" or "refeeding cells"), since iPSC's factors such as FGF2 require a short half-life. Stem cells must typically be fed every 24 hours. The frequency of a "medium change" can vary, and depends on the growth rate or the division ratio of the cells. The times of the confluence scan can likewise depend on the growth rate of the cells, so that a confluence scan can take place before or after a first or second media change, for example.

The above statements characterize the effective function as a function to be minimized, for example if the effective function represents costs. However, the reverse case is also possible, for example when the effective function represents a benefit. Then, the respective effective function is to be maximized.

BRIEF DESCRIPTION OF THE DRAWINGS

Exemplary embodiments of the invention will be described below based upon the attached drawings. Shown on:

FIG. 1 in the upper section marked "a" are three applications A1, A2, A3 with respective associated workflows W1.1, W1.2, W1.3, W2.1, W2.2, W2.3 and W3.1, W3.2 and W3.3, which are to be performed at preferred start times, wherein the workflows W2.1, W2.2 and W2.3 of application A2 must be performed at fixed (invariably set) start times, in the lower section marked "b" are the workflows of the three applications after they have been partially shifted in time (see arrows) and arranged in such a way that they can be performed one after the other in a process module, FIG. 2 in the upper section marked "a" is an effective function W(t), in the section marked "b" lying thereunder is a timescale in days, and in the lower section marked "c" are the confluence values corresponding to the timescale, FIG. 3 is a calculation scheme for calculating the earliest start time ($t_e$), the preferred start time ($t_p$) and the latest start time ($t_l$), FIG. 4 is a calculation scheme, likewise for calculating the preferred start time from the result of a confluence scan, FIG. 5 is an illustration of an effective function W(t) according to the section in FIG. 2 marked with an "a,"

FIG. 6 is another illustration of an effective function W(t) according to the section in FIG. 2 marked with an "a,"

FIG. 7 is an application A that contains three workflows W1, W2, W3, which are cyclically repeated, FIG. 12 is an illustration according to FIG. 1, in which two workflows W2.1 and W3.1 have been swapped in their chronological order in order to optimize the effective function, for example maximizing or minimizing, and FIG. 13 is an illustration according to FIG. 2, but for a case in which the effective function indicates a benefit and is to be maximized.

DETAILED DESCRIPTION OF THE EMBODIMENTS

Figure 8:
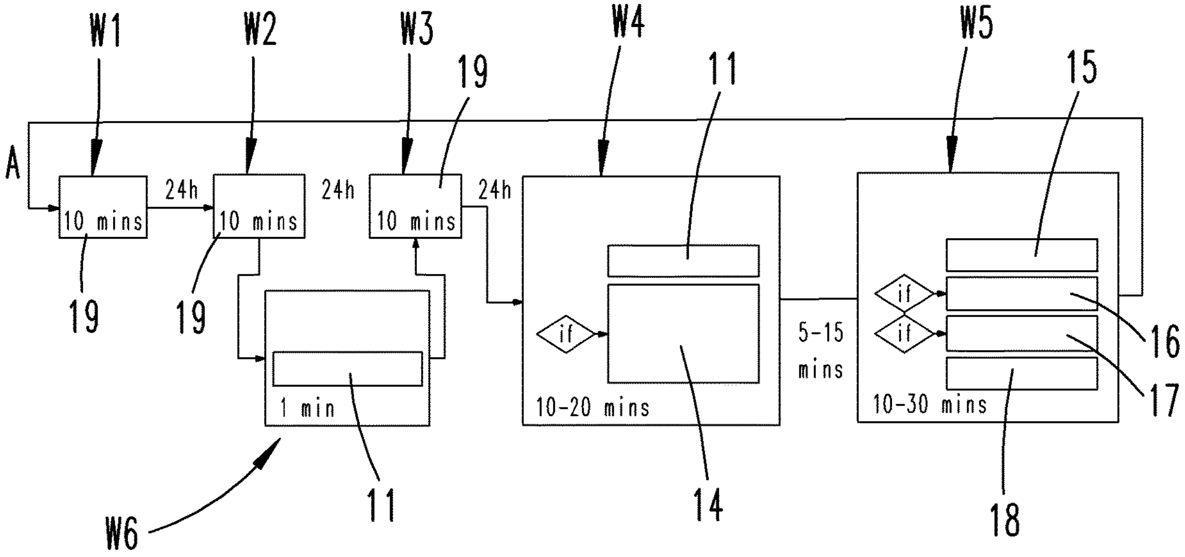
FIG. 8 is an application A that contains five workflows W1, W2, W3, W4, W5, which are cyclically repeated, FIG. 9 schematically are the steps for resolving a time conflict, when two or more workflows are to be performed simultaneously, or the start time of one workflow falls within a time period during which another workflow is to be performed, FIG. 10 schematically are the elements of a system according to the invention, FIG. 11 schematically is a graphical user interface for manually configuring an effective function.

FIG. 10 schematically depicts a system consisting of a storage module 2 for storing cell cultures. Storage modules 2 such as these can be incubators. The housing of such a storage module can incorporate several "hotels," in which a plurality of carriers 1 are stored one above the other. Reference is made to WO 2020/098960 A1 with regard to such storage modules 2.

A transport device 5 is provided, which can have a gripper, end effector and/or other transport means, for example transport rails or an automatization mechanism, with which a carrier 1 can be transported from the storage module 2 to a process module 3. Reference is made to WO 2020/098957 A1 with regard to the configuration of a process module. One or more treatment devices 4 are located in the process module 3. The treatment device 4 can have a microscope, a pipetting device, or the like.

The preferably several carriers 1 stored in a storage module 2 can be microplates. Such microplates have a plurality of troughs, in which a respective nutrient with cell cultures is stored. Each carrier 1 can have cell cultures of a cell type. Different carriers 1 can carry different cell lines. The storage module 2 is configured in such a way that the cells stored there reproduce at a cell-specific division rate.

A control device 6 can have a microcontroller or a microcomputer, which is able to control the transport device 5 and the treatment device 4. The control device 6 can additionally have a memory device 7, in which applications are stored in digital form. An application is a treatment specification for treating cell cultures, in which case it can be provided that each carrier 1 be assigned an application, i.e., a treatment specification, which takes into account the peculiarities of the cell line carried by the carrier 1. However, an application A can also comprise several carriers 1, in which case it is then provided in particular that the several carriers 1 carry cells of the same type. The storage module 2 can be stored with carriers 1 that each carry different cell culture lines, and have assigned to them a respective different application A1, A2, A3. Each application can have one or more workflows W1, W2, W3, W4, W5, in which each workflow can contain one or more work steps. The workflows of an application A1, A2, A3 are to be performed one after the other in defined time intervals, with each workflow W1, W2, W3 having a preferred start time at which it can be started. However, some or all of the workflows W1, W2, W3 can also be started at an earlier time or at a later time, but not before an earliest start time $t_e$ and not after a latest start time $t_l$. There can be times of between minutes and days between the workflows of an application. There are preferably times of between a few seconds and six days, half to six days or one to four days between the workflows. The duration of a workflow can measure between one minute and 60 minutes.

A workflow includes one or more work steps that must be performed immediately or shortly after the other, in which a pause between two consecutive work steps is preferably zero or can often last for a few minutes, with no other workflow occurring in between. For example, a work step can be a confluence scan 11, in which a measured confluence 12 is ascertained so as to determine a preferred start time $t_p$ therefrom. Additional work steps can involve adding a detachment agent 14, suspending cells 15, centrifuging, counting living or dead cells 17, creating cells, i.e., seeding new cells 18, adding nutrients, i.e., feeding cells 19. A workflow can comprise at least one of these work steps or one that has not been previously listed.

The applications having one or more workflows W1, W2, W3, W4, W5 can be performed periodically over an indefinite period of time, for example to maintain cell lines. An application can extend over several days.

The system can have several instances of the same application, for example the cell line maintenance application can have a first instance "maintain CHO cells" or a second instance "maintain Vero cells."

FIG. 7 shows an application A consisting of three workflows W1, W2, W3, in which a first workflow W1 is performed after the start of the application after one to three days, in which a confluence scan 11 is performed. After another one to three days, a second workflow W2 is performed, in which a confluence scan 11 is likewise initially performed, and the cells are washed and a detachment agent 14 is added depending on the degree of confluence so as to detach the cells from the bottom of a depression in the carrier. While the confluence scan 11 lasts for about 1 minute, the next step, for example washing or adding detachment agent 14, can take 10 to 20 minutes. An output confluence can be measured in the first workflow W1. The additional measurement of confluence that took place in the second workflow W2 can be used to determine the division rate of the cell line. The preferred start time $t_p$ of another workflow can be calculated from that, for example if the expected confluence measures 80%.

A third workflow W3 can also be performed after five to ten minutes. This workflow can involve the steps of removing the cells 15, centrifuging 16, counting the living and dead cells 17 and/or seeding cells 18, or seeding cells in new microplates 18.

FIG. 8 shows another exemplary embodiment of an application in which five workflows W1, W2, W3, W4, W5 are performed one after the other, and the sequence of five workflows is repeated for an indefinite period of time.

Workflow W1, workflow W2 and workflow W3 can each contain a nutrient addition 19. Workflow W6 includes the confluence scan step 11. The interval between nutrient additions can be set to 24 hours, for example, and the cell doubling time can vary between the cell lines, so that the number of nutrient additions depends on the growth rate of the cells, i.e., the number of workflows in the application can vary. Depending on the start time of the confluence scan 11 and growth rate of the cells, the sequence of workflows W1, W2, W3 and W6 can also vary (i.e., W6 can take place outside of the sequence shown on FIG. 8). Workflow W4 comprises the confluence scan 11, and step 14 comprises medium removal and detachment agent addition. Work sequence 5 can involve suspending the cells in step 15, centrifuging in step 16, counting the dead and living cells in step 17, and seeding the cells in step 18.

FIGS. 2, 5 and 6 show exemplary progressions of an effective function W(t). The effective function reflects a value that depends on the start time t of a workflow W1, W2, W3, W4, W5. The effective function W(t) has a minimum at a preferred start time $t_p$ of the workflow, to which the effective function is assigned. The effective function has a maximum at a time that corresponds to the latest start time $t_l$ or the earliest start time $t_e$.

Section "b" of FIG. 2 provides an example of the number of days to which the start times indicated in section "a" relate. Section "b" of FIG. 2 expresses the accompanying confluences, meaning the degree of coverage of the bottom of a trough in which the cell culture is stored, in percentages. The optimal start time is the time at which the expected confluence measures 80%. The latest start time is the time at which the confluence still remains under 100%. The earliest start time $T_e$ is the time at which the expected confluence measures about 20 to 30%.

The control device 6 is programmed in such a way that, in a conflict-free case, each workflow W1, W2, W3, W4, W5 begins at the preferred start time $t_p$. In case of a conflict, in which two or more workflows would have to take place simultaneously according to the timetables prescribed by applications A1, A2, A3, the workflows are shifted in time in such a way that they can be performed in sequence one after the other in the same process module 3. To this end, the workflows are shifted in time in such a way that the sum of effective functions has a minimum or is minimal. This type of shift in time can involve a change in the sequence, i.e., a rearrangement of workflows (work processes).

FIG. 13 shows an example of an effective function to be maximized in an illustration according to FIG. 2.

FIG. 1 shows an example in which three applications A1, A2, A3 each have three workflows W1.1, W1.2, W1.3; W2.1, W2.2, W2.3 and W3.1, W3.2 and W3.3. Workflows W1.1, W2.1 and W3.1 of applications A1, A2, A3 are timed in such a way that they would overlap when performed as planned. Workflows W2.1, W2.2, W2.3 of application A2 have the additional peculiarity that they can only be formed at the preferred start time, so that the latest start time and earliest start time are to some extent identical. These workflows W2.1, W2.2 and W2.3 to some extent govern the chronological arrangement of the remaining workflows. As a consequence, a system according to the invention can comprise those workflows W2.1, W2.2, W2.3 that govern the chronological arrangement of the remaining workflows.

As a consequence thereof, workflow W1.1 is shifted forward in time and workflow W3.1 is shifted backward in time in order to minimize the sum of effective functions of workflows W1.1, W2.1 and W3.1.

The respective second workflows W2.2 and W3.2 do not have to be shifted in time in the exemplary embodiment, since they can be performed one after the other as scheduled. Only workflow W1.2 must be shifted slightly forward. None of workflows W1.3, W2.3 and W3.3 have to be shifted in time. While the sequence of workflows changes in the example shown, it is expected that minimizing or maximizing the sum of effective functions can in some instances lead to a change in the workflow sequence.

FIG. 12 shows that it can also be possible to swap workflows W3.1 and W2.1.

FIG. 3 shows a curve for the reproduction rate of a cell culture as a function of time. The time of the preferred start of a workflow $t_p$ is selected in such a way that the expected confluence then measures 80%. The time of the latest possible start $t_l$ of the workflow is selected in such a way that the expected confluence then measures 90%. The time of the earliest start $t_e$ of the workflow is selected in such a way that the expected confluence then measures 20%.

FIG. 4 shows the way to calculate a calculated, preferred start time 13 with the help of a confluence 12 measured at the time of a confluence scan 11. A confluence of 60% was measured at the time of the confluence scan 11. The point on the growth curve at which the confluence measures 80% is determined.

In this example, the system counts the resuspended cells, e.g., if a workflow was previously performed, and calculates a dilution so as to set a confluence of 10% of the cells. Proceeding from this set 10%, the system then calculates the time at which the cells would be expected to be located in the middle or at the end of a growth cycle (50 to 80% confluence). Assuming an exponential growth curve, for example, the time at which the confluence measures an exemplary 80% is calculated from the initial confluence, e.g., of 10%.

For a case in which the system does not know the doubling time of the cells, it can conservatively use the shortest known doubling time for mammalian cells in a culture or a doubling time that is less than the shortest known doubling time. For example, the system can use a preliminary doubling time of 12 hours, so as to calculate when the confluence scan is to be performed. Alternatively, however, the system can also perform a confluence scan only every 24 hours, until the cells have reached a stable doubling time. As soon as the system has data about the doubling time, it can use the doubling time of the cells to determine when an 80% confluence has been reached.

FIGS. 5 and 6 show variants of the effective function for which the effective function W(t) has a nonlinear progression. In the effective function shown on FIG. 5, the time interval between the latest start time $t_l$ and the preferred start time $t_p$ is significantly smaller than the time interval between the earliest start time $t_e$ and the preferred start time $t_p$.

By contrast, FIG. 6 shows a progression of the effective function W(t) that is symmetrical relative to $t_p$.

FIG. 11 shows an example of a graphical interface with which the progression of the effective function W(t) can be manually preset by "dragging" anchor points on a display screen.

It may be desired that users be able to add applications, workflows, or other work processes to the system, which can constitute a challenging planning problem to be handled by the system. Times of a timetable can be changed. In particular, it can be considered that some cell lines grow more quickly or slowly than expected. During a workflow, one or more carrier plates can be treated one immediately after the other with the treatment device 4. This preferably takes place with the same work steps.

According to the invention, a cell culture system is prepared. In one implementation, the cell culture system has an incubator, a refrigerator, two storages for laboratory equipment at room temperature and a processing module 3. The process module 3 can have a liquid handler, for example a pipette. Other mechanisms can be provided, for example a decapper for uncapping bottles, a gripper for handling carriers 1, along with a microscope. Depending on the applications and workflows or other work processes, the capacity of the system can be limited either by the capacity of the incubator for the carriers, in particular carrier plates, and in particular the number of plates that the incubator can process, or by the capacity (speed) of the process module. As a consequence, only a limited number of work processes or workflows is possible in a process module 3.

The system can perform applications that involve the maintenance of cell lines or a cell-based "assay" or an experiment, for example. The applications can run for an indeterminate time with respect to cell line maintenance, and in particular extend over days or weeks.

In particular, the workflows comprise the "confluence scan," addition of a "detachment agent" and cell removal. The cell removal workflow can contain individual operations, specifically the removal of cells and the seeding of cells. Work steps such as centrifugation or the counting of dead and living cells can further be provided. In order to cultivate a specific cell line, e.g., CHO cells, an instance of the application is generated that contains the parameter for cultivating this cell line. Parameters can include the complete medium recipe, passage confluence, split ratio, or number of carriers, for example carrier plates like microplates.

The work steps within a workflow are interrelated, and have no gaps and in particular no gaps of more than one minute between two work steps. The time between two workflows in the same application is greater than one minute, and typically measures minutes, hours, or days. The transport of a carrier from the storage module 2 to the process module 3 and its treatment there can be delayed if the confluence required for this purpose has not yet been reached. As a consequence, a workflow can contain work steps that are optionally performed, for example when a confluence scan reaches a specific value. If the specific value is not reached in the confluence scan, one or more ensuing work steps can be omitted or delayed.

Figure 9:
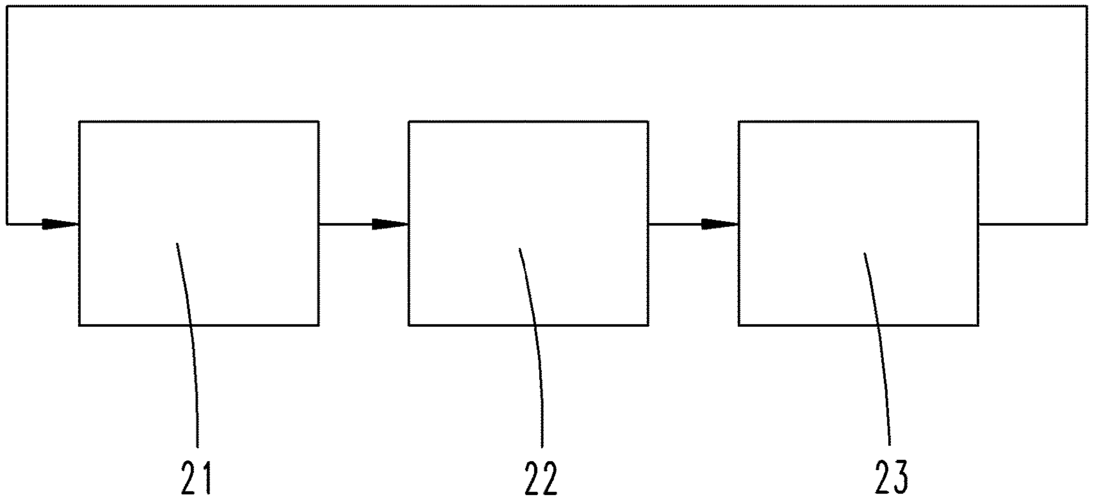

The method underlying the system according to the invention is able to process a timetable in which the duration and intervals of the workflows differ from each other. The method can be summarized as follows, with reference to FIG. 9:

Defining a workflow at a preferred starting point $t_p$, an earliest start time $t_e$ and a latest start time $t_l$, as well as the costs for performing the workflow at a start time other than $t_p$, wherein the costs are represented in the effective function W(t) (performing the workflow 21).

If an entry was made by a user or if data are found that would alter the preferred start time of an ensuing workflow, for example, the data (start times) of all ensuing workflows are recalculated (22). The calculation takes place in such a way that a sum, in particular an overall sum of the effective functions of the workflows, assumes a minimum (23). The minimum need not be a global minimum, and can be a local minimum.

The sum Σ of all effective functions W(t) of all workflows can be represented as a multidimensional function.

$$\sum = W_1(t_1) + W_2(t_2) + \ldots + W_n(t_n)$$

Based on the shift in the respective start times and taking into account the duration of each workflow, this makes it possible to calculate a global or local minimum $$\frac{d}{dt}\Sigma = 0$$

which is subject to the boundary condition that all workflows follow each other in time, and that the start time of each of the workflows does not lie in any duration of another workflow.

The invention provides a method for mixing the workflows, in which a sum of effective functions W(t) is minimized, for example which represents the costs to be expended for performing the workflows, so that the method according to the invention is a cost-optimized method.

As a consequence, the method relates to a planner or a planning software, with which a plurality of applications (applications) can be managed, wherein each application contains one or more workflows (work processes). The work processes of the different applications are performance optimized, wherein the optimization characters described above are used.

The above statements serve to explain the inventions covered by the application as a whole, which each also independently advance the prior art at least by the following feature combinations, wherein two, several or all of these feature combinations can also be combined, specifically:

A system, characterized in that each workflow W1.1, W1.2, W1.3; W2.1, W2.2, W2.3; W3.1, W3.2, W3.3 has assigned to it an effective function W(t) that depends on the start time t, and the sequence and start times (t) of the workflows W1.1, W1.2, W1.3; W2.1, W2.2, W2.3; W3.1, W3.2, W3.3 of different applications A1, A2, A3 are calculated by minimizing the sum Σ of effective functions W(t).

A method, characterized in that each workflow W1.1, W1.2, W1.3; W2.1, W2.2, W2.3; W3.1, W3.2, W3.3 has assigned to it an effective function W(t) that depends on the start time t, and the sequence and start times (t) of the workflows W1.1, W1.2, W1.3; W2.1, W2.2, W2.3; W3.1, W3.2, W3.3 of different applications A1, A2, A3 or instances of the same application are calculated by minimizing the sum Σ of effective functions W(t).

A system or a method, characterized in that each workflow W1.1, W1.2, W1.3; W2.1, W2.2, W2.3; W3.1, W3.2, W3.3 has assigned to it a preferred start time $t_p$, at which the effective function W(t) assigned to the workflow W1.1, W1.2, W1.3; W2.1, W2.2, W2.3; W3.1, W3.2, W3.3 has a minimum.

A system or a method, characterized in that at least some first workflows W1.1, W1.2, W1.3 of the different applications A1, A2, A3 have a first preferred start time $t_p$, which fall within a treatment duration of a second workflow whose second preferred start time $t_p$ lies before the first preferred start time $t_p$, wherein the control device 6 shifts the first and/or second start time in such a way that the two first and second workflows W1.1, W1.2, W1.3; W2.1, W2.2, W2.3; W3.1, W3.2, W3.3 are performed one after the other, wherein the first and second start times are selected in such a way as to minimize or maximize the sum Σ of effective functions W(t).

A system or a method, characterized in that at least some of the workflows W2.1, W2.2, W2.3 have assigned to them an earliest start time $t_e$, before which the workflow W2.1, W2.2, W2.3 must not be started and/or a latest start time $t_l$ after which the workflow W2.1, W2.2, W2.3 must not be started, wherein it is provided in particular that the effective function W(t) has a maximum at the earliest start time $t_e$ and at the latest start time $t_l$.

A system or a method, characterized in that the effective function W(t) has a branch that linearly or nonlinearly descends or ascends from an earliest start time $t_e$ to the preferred start time $t_p$ and a branch that linearly or nonlinearly ascends or descends from the preferred start time $t_p$ to the latest start time $t_l$.

A system or a method, characterized in that the progression of the effective function W(t) is selected in such a way that the costs to be expended for performing the application A1, A2, A3 at the start of the workflows W1.1, W1.2, W1.3; W2.1, W2.2, W2.3; W3.1, W3.2, W3.3 have a minimum at the preferred start times $t_p$ and a respective maximum at the earliest and latest start times.

A system or a method, characterized in that at least some of the workflows W1.1, W2.1, W3.1 have a monitoring step that monitors cell growth, in which the confluence of a cell culture is determined, and the preferred start time $t_p$ of at least one ensuing workflow W1.1, W2.2, W3.3 is determined depending thereupon, and/or that the earliest start time $t_e$ and/or the latest start time $t_l$ of an ensuing workflow W1.2, W2.2, W3.2 is determined in the monitoring step.

A system or a method, characterized in that the workflow W1.1, W1.2, W1.3; W2.1, W2.2, W2.3; W3.1, W3.2, W3.3 comprises at least one or more of the following work steps: Creating a cell culture 18, counting the living or dead cells 17, removing cells of the cell culture, detaching the cells from the bottom of a trough of the carrier 1, adding a detachment agent 14, confluence scan 11, adding a nutrient 19 or discontinuing the cell culture 15 or seeding cells.

A system or a method, characterized in that the transport device 5 removes a first carrier 1 for performing a first workflow W1.1 from a storage space in the storage module 2 at a first time and transports it to the process module 3 in such a way that the treatment device 4 begins to treat the cell culture carried by the first carrier at a first start time t, and the transport device 5 then removes a second carrier 1 for performing a second workflow 2.1 from a storage space in the storage module 2 at a second time and transports it to the process module 3 in such a way that the treatment device 4 begins to treat the cell culture carried by the second carrier 1 at a second start time t after the performance of the first workflow W1.1 has concluded, wherein the two start times t are calculated in such a way as to minimize or maximize the sum Σ of the effective functions W(t).

A system or a method, characterized by a graphic data input device, with which a user can set the progression of an effective function.

A system or a method, characterized in that the treatment device 4 has a pipetting device, a microscope and/or an opening device for opening nutrient-containing containers, and /or that the storage module 2 is an incubator, and/or that the transport device 5 has a gripping arm or end effector and/or is automated.

A system or a method, characterized in that the minimum or maximum is a local minimum or maximum, and/or that the minimum or maximum is a value calculated over the duration of a limited number of workflows W1.1, W1.2, W1.3; W2.1, W2.2, W2.3; W3.1, W3.2, W3.3.

All disclosed features (whether taken separately or in combination with each other) are essential to the invention. The disclosure of the application hereby also incorporates the disclosure content of the accompanying/attached priority documents (copy of the prior application) in its entirety, also for the purpose of including features of these documents in claims of the present application. Even without the features of a referenced claim, the subclaims characterize standalone inventive further developments of prior art with their features, in particular so as to submit partial applications based upon these claims. The invention indicated in each claim can additionally have one or more of the features indicated in the above description, in particular those provided with reference numbers and/or indicated on the reference list. The invention also relates to design forms in which individual features specified in the above description are not realized, in particular if they are recognizably superfluous with regard to the respective intended use, or can be replaced by other technically equivalent means.

Reference List

| | | | |
|---|---|---|---|
| 1 | Carrier | W1.1 | Workflow |
| 2 | Storage module | W1.2 | Workflow |
| 3 | Process module | W1.3 | Workflow |
| 4 | Treatment device | W2.1 | Workflow |
| 5 | Transport device | W2.2 | Workflow |
| 6 | Control device | W2.3 | Workflow |
| 7 | Memory device | W3.1 | Workflow |
| 11 | Confluence scan | W3.2 | Workflow |
| 12 | Measured confluence | W3.3 | Workflow |
| 13 | Calculated preferred | W1 | Workflow |
| | start time | W2 | Workflow |
| 14 | Adding a detachment | W3 | Workflow |
| | agent | W4 | Workflow |
| 15 | Suspending the cells | W5 | Workflow |
| 16 | Centrifuging | W(t) | Effective |
| 17 | Counting | | |
| 18 | Seeding cells | t | Start time |
| 19 | Adding nutrient | $t_e$ | Earliest |
| 21 | Performing a workflow | $t_p$ | Preferred |
| 22 | Recalculating $t_e$, $t_p$, $t_l$ | $t_l$ | Latest start |
| 23 | Shifting in time | Σ | Sum |
| A | Application | | |
| A1 | Application | | |
| A2 | Application | | |
| A3 | Application | | |

What is claimed is:

1. A system for cultivating biological cell cultures, the system comprising:

a plurality of carriers (1), each for carrying one or more cell cultures;

a storage module (2) for storing the carriers (1);

a process module (3) within which the cell cultures carried by the carriers (1) are treated by a treatment device (4);

a transport device (5) for transporting the carriers (1) between the storage module (2) and the process module (3); and a control device (6) with a memory device (7), the control device (6) for controlling the transport device (5) and the treatment device (4), wherein applications (A1, A2, A3) are stored in the memory device (7), each of the applications (A1, A2, A3) being assigned to a corresponding one of the one or more cell cultures;

wherein each of the applications (A1, A2, A3) is a treatment specification for treating the cell culture to which the application (A1, A2, A3) is assigned, wherein each of the applications (A1, A2, A3) contains one or more workflows (W1.1, W1.2, W1.3; W2.1, W2.2, W2.3; W3.1, W3.2, W3.3) that are performed in the process module (3) at successive time intervals, each with a respective start time (t), wherein each of the workflows (W1.1, W1.2, W1.3; W2.1, W2.2, W2.3; W3.1, W3.2, W3.3) contains one or more work steps to be performed one after another, wherein the control device (6) controls a parallel execution of the applications (A1, A2, A3), and thereby starts one or more of the workflows (W1.1, W1.2, W1.3; W2.1, W2.2, W2.3; W3.1, W3.2, W3.3) from different ones of the applications (A1, A2, A3) in chronological order one after another in the process module (3), wherein each of the workflows (W1.1, W1.2, W1.3; W2.1, W2.2, W2.3; W3.1, W3.2, W3.3) is assigned an effective function W(t) that depends on the respective start time (t) and represents costs for performing the workflow (W1.1, W1.2, W1.3; W2.1, W2.2, W2.3; W3.1, W3.2, W3.3) at the respective start time (t), wherein for each of the workflows (W1.1, W1.2, W1.3; W2.1, W2.2, W2.3; W3.1, W3.2, W3.3), performing the workflow (W1.1, W1.2, W1.3; W2.1, W2.2, W2.3; W3.1, W3.2, W3.3) at a time other than a corresponding preferred start time ($t_p$) increases the effective function W(t) assigned to the workflow (W1.1, W1.2, W1.3; W2.1, W2.2, W2.3; W3.1, W3.2, W3.3), and wherein an order and the respective start times (t) of the workflows (W1.1, W1.2, W1.3; W2.1, W2.2, W2.3; W3.1, W3.2, W3.3) of different ones of the applications (A1, A2, A3) or duplicate instances of one of the applications are calculated by minimizing a first sum (Σ) of the respective effective functions (W(t)) assigned to the workflows (W1.1, W1.2, W1.3; W2.1, W2.2, W2.3; W3.1, W3.2, W3.3).

2. The system of claim 1, wherein the transport device (5) is configured to remove a first one of the carriers (1) for performing a first one of the workflows (W1.1) from a storage space in the storage module (2) at a first time and transport the first carrier (1) to the process module (3) so that the treatment device (4) begins to treat a cell culture carried by the first carrier (1) at a first start time (t), and the transport device (5) is configured to remove a second one of the carriers (1) for performing a second one of the workflows (W2.1) from the storage space in the storage module (2) at a second time and transport the second carrier (1) to the process module (3) so that the treatment device (4) begins to treat a cell culture carried by the second carrier (1) at a second start time (t) after the first workflow (W1.1) has concluded, wherein the first and second start times (t) are calculated so as to minimize a second sum (Σ) of the respective effective functions (W(t)) assigned to the first workflow (W1.1) and the second workflow (W2.1).

3. The system of claim 1, further comprising a graphical data input device for a user to configure a progression of one of the effective functions (W(t)).

4. The system of claim 1, wherein at least one of:

(i) the treatment device (4) has one or more of a pipetting device, a microscope or an opening device for opening nutrient-containing containers, (ii) the storage module (2) is an incubator, (iii) the transport device (5) has a gripping arm or end effector, or (iv) the transport device (5) is automated.

5. The system of claim 1, wherein at least one of:

(i) a minimum of the first sum (Σ) is a local minimum; or (ii) the minimum of the first sum (Σ) is a value calculated over a duration of a subset of the workflows (W1.1, W1.2, W1.3; W2.1, W2.2, W2.3; W3.1, W3.2, W3.3).

6. A method for cultivating biological cell cultures, the method comprising:

carrying cell cultures in a plurality of carriers (1), each carrying one or more of the cell cultures;

storing the carriers (1) in at least one storage module (2);

treating the cell cultures in a process module (3) by a treatment device (4);

transporting the carriers (1) with a transport device (5) between the storage module (2) and the process module (3);

controlling, by a control device (6) having a memory device (7), the transport device (5) and the treatment device (4); and storing applications (A1, A2, A3) in the memory device (7), each of the applications (A1, A2, A3) being assigned to a corresponding one of the cell cultures, wherein each of the applications (A1, A2, A3) is a treatment specification for treating the cell culture to which the application (A1, A2, A3) is assigned, wherein each of the applications (A1, A2, A3) contains one or more workflows (W1.1, W1.2, W1.3; W2.1, W2.2, W2.3; W3.1, W3.2, W3.3) that are performed in the process module (3) at successive time intervals, each with a respective start time (t), wherein each of the workflows (W1.1, W1.2, W1.3; W2.1, W2.2, W2.3; W3.1, W3.2, W3.3) contains one or more work steps to be performed one after another, wherein the control device (6) controls a parallel execution of the applications (A1, A2, A3), and thereby starts one or more of the workflows (W1.1, W1.2, W1.3; W2.1, W2.2, W2.3; W3.1, W3.2, W3.3) from different ones of the applications (A1, A2, A3) in chronological order one after another in the process module (3), wherein each of the workflows (W1.1, W1.2, W1.3; W2.1, W2.2, W2.3; W3.1, W3.2, W3.3) is assigned an effective function W(t) that depends on the respective start time (t) and represents costs for performing the workflow (W1.1, W1.2, W1.3; W2.1, W2.2, W2.3; W3.1, W3.2, W3.3) at the respective start time (t), wherein for each of the workflows (W1.1, W1.2, W1.3; W2.1, W2.2, W2.3; W3.1, W3.2, W3.3), performing the workflow (W1.1, W1.2, W1.3; W2.1, W2.2, W2.3; W3.1, W3.2, W3.3) at a time other than a corresponding preferred start time ($t_p$) increases the effective function W(t) assigned to the workflow (W1.1, W1.2, W1.3; W2.1, W2.2, W2.3; W3.1, W3.2, W3.3), and wherein an order and the respective start times (t) of the workflows (W1.1, W1.2, W1.3; W2.1, W2.2, W2.3; W3.1, W3.2, W3.3) of different ones of the applications (A1, A2, A3) or duplicate instances of one of the applications are calculated by minimizing a first sum (Σ) of the respective effective functions (W(t)) assigned to the workflows (W1.1, W1.2, W1.3; W2.1, W2.2, W2.3; W3.1, W3.2, W3.3).

7. The method of claim 6, wherein, for each of the workflows (W1.1, W1.2, W1.3; W2.1, W2.2, W2.3; W3.1, W3.2, W3.3), the corresponding preferred start time ($t_p$) is a start time at which the effective function (W(t)) assigned to the workflow (W1.1, W1.2, W1.3; W2.1, W2.2, W2.3; W3.1, W3.2, W3.3) has a minimum.

8. The method of claim 7, wherein a first one of the workflows (W1.1, W1.2, W1.3) has a first preferred start time ($t_p$) which falls within a treatment duration of a second workflow with a second preferred start time ($t_p$) that lies before the first preferred start time ($t_p$), wherein the control device (6) shifts the start time of the first workflow and the start time of the second workflow so that the first and second workflows (W1.1, W1.2, W1.3; W2.1, W2.2, W2.3; W3.1, W3.2, W3.3) are performed one after the other, and wherein the start time of the first workflow and the start time of the second workflow are selected so as to minimize a second sum (Σ) of the respective effective functions (W(t)) assigned to the first and second workflows.

9. The method of claim 7, wherein a first one of the workflows (W2.1, W2.2, W2.3) has an earliest start time ($t_e$) before which the first workflow (W2.1, W2.2, W2.3) must not be started and a latest start time ($t_l$) after which the first workflow (W2.1, W2.2, W2.3) must not be started, and wherein the effective function (W(t)) assigned to the first workflow (W2.1, W2.2, W2.3) has a maximum at the earliest start time ($t_e$) and at the latest start time ($t_l$).

10. The method of claim 7, wherein the effective function (W(t)) assigned to a first one of the workflows has a first segment that decreases between an earliest start time ($t_e$) and the preferred start time ($t_p$) of the first one of the workflows and a second segment that increases between the preferred start time ($t_p$) of the first one of the workflows and a latest start time ($t_l$) of the first one of the workflows.

11. The method of claim 6, wherein the effective function (W(t)) of a first one of the workflows has a minimum at the preferred start time ($t_p$) of the first one of the workflows and respective maxima at an earliest start time ($t_e$) and a latest start time ($t_l$) of the first one of the workflows.

12. The method of claim 6, wherein a first one of the workflows (W1.1, W2.1, W3.1) has a monitoring step that monitors cell growth, in which a confluence of a cell culture is determined, and at least one of:

(i) a preferred start time ($t_p$) of a second one of the workflows (W1.2, W2.2, W3.2) following the first workflow (W1.1, W2.1, W3.1) is determined depending on the confluence of the cell culture, or (ii) one or more of an earliest start time ($t_e$) or a latest start time ($t_l$) of the second workflow (W1.2, W2.2, W3.2) following the first workflow (W1.1, W2.1, W3.1) is determined in the monitoring step.

13. The method according to claim 6, wherein a first one of the workflows (W1.1, W1.2, W1.3; W2.1, W2.2, W2.3; W3.1, W3.2, W3.3) comprises one or more of creating one of the cell cultures (18), counting a number of living or dead cells (17) in one of the cell cultures, removing cells from one of the cell cultures, detaching the cells from a bottom of a trough of the carrier (1), adding a detachment agent (14) to one of the cell cultures, performing a confluence scan (11) of one of the cell cultures, adding a nutrient (19) to one of the cell cultures, discontinuing one of the cell cultures (15) or seeding cells.

14. A non-transitory machine-readable medium comprising instructions that, when executed by a processor, cause the processor to perform the method of claim 6.

* * * * *